(12) United States Patent
Harada et al.

(10) Patent No.: US 6,586,457 B2
(45) Date of Patent: Jul. 1, 2003

(54) METHODS FOR INHIBITING BONE RESORPTION

(75) Inventors: Shun-Ichi Harada, North Wales, PA (US); Mohamed MacHwate, Landsdale, PA (US); Gideon A. Rodan, Bryn Mawr, PA (US); Marc Labelle, St. Lazare (CA); Kathleen Metters, Montreal (CA); Robert N. Young, Senneville (CA)

(73) Assignees: Merck & Co., Inc., Rahway, NJ (US); Merck Frosst Canada & Co., Nova Scotia (CA)

( * ) Notice: Subject to any disclaimer, the term of this patent is extended or adjusted under 35 U.S.C. 154(b) by 0 days.

(21) Appl. No.: 09/817,424

(22) Filed: Mar. 26, 2001

(65) Prior Publication Data

US 2001/0012838 A1 Aug. 9, 2001

Related U.S. Application Data

(62) Division of application No. 09/416,733, filed on Oct. 13, 1999, now Pat. No. 6,414,006.
(60) Provisional application No. 60/104,339, filed on Oct. 15, 1998.

(51) Int. Cl.$^7$ .................... A61K 31/41; A61K 31/40; A61K 31/19; A61K 31/557; A61K 31/66

(52) U.S. Cl. .................... 514/384; 514/383; 514/424; 514/461; 514/573

(58) Field of Search ................ 514/384, 108, 514/424, 461, 573

(56) References Cited

U.S. PATENT DOCUMENTS

| | | |
|---|---|---|
| 3,982,016 A | 9/1976 | Walsh |
| 4,000,309 A | 12/1976 | Walsh |
| 4,018,892 A | 4/1977 | Walsh |
| 4,342,756 A | 8/1982 | Collington et al. |
| 4,782,082 A | 11/1988 | Kreutner et al. |
| 5,310,759 A | 5/1994 | Bockman |
| 5,366,965 A | 11/1994 | Strein |
| 5,411,980 A | 5/1995 | Ashton et al. |
| 5,616,571 A | 4/1997 | Daifotis et al. |
| 5,646,134 A | 7/1997 | Yates |
| 5,730,715 A | 3/1998 | Sage, Jr. et al. |
| 5,858,778 A | 1/1999 | Alnemri et al. |
| 5,892,099 A | 4/1999 | Maruyama et al. |

FOREIGN PATENT DOCUMENTS

| | | |
|---|---|---|
| WO | WO 97/31640 | 9/1997 |
| WO | WO 98/27976 | 7/1998 |

OTHER PUBLICATIONS

Harada et al., Connective Tussue Res., vol. 31 (1995), pp. 279–282, "The role of prostaglandins in bone formation".

Ono et al., J. of Endoc., vol. 158 (1998), pp. R1–R5, "Important role of EP4, a subtype of prostaglandin (PG) E reeptor, in osteoclast–like cell formation from mouse bone marrow cells induced by PGE2".

Jee et al., Bone vol. 21 (1997), pp. 297–304, "The in vivo anabolic actions of prostaglandins in bone".

Ross, Goodman & Gilman's The Pharmacol. Basis of Therapeutics, 9th ed., (1996), Chap. 2, "Pharmacodynamics: Mechanisms of drug action and the relationship between drug concentration and effect", pp. 29–41.

Luckman et al., J. of Bone and Min. Res., vol. 13 (1998), "Heterocycle–containing bisphosphonates cause apoptosis and inhibit bone resorption by preventing protein prenylation: Evidence from structure–activity relationships in J774 macrophages", pp. 1668–1678.

Weinstein et al., J. of Clin. Investig., vol. 102 (1998), pp. 274–282, "Inhibition of osteoblastogenesis and promotion of apoptosis of osteoblasts and osteocytes by glucocorticoids".

Grigoriadis et al., Differentiation, vol. 60 (1996), pp. 299–307, "Analysis of chondroprogenitor frequency and cartilage differentiation in a novel family of clonal chondrogenic rat cell lines".

Nakahara et al., Bone, vol. 11 (1990), pp. 181–188. "Bone and cartilage formation in diffusion chambers by subcultured cells derived from the periosteum".

Funk et al., J., of Biol. Chem., vol. 268 (1993), pp. 26767–26772, "Cloning and expression of a cDNA for the human prostglandin E receptor EP1 subtype".

Regan et al., Prostaglandins, vol. 47 (1994), pp. 151–168, "Cloning of a novel human prostaglandin receptor with characteristics of the pharmacologically defined EP2 subtype".

Yang et al., Biochem. & Biophys. Res. Comm., vol. 198 (1994), pp. 999–1006, "Cloning, and expression of the EP3–subtype of human receptors for prostaglandin E2".

Bastien et al., J. of Biol. Chem., vol. 269 (1994), pp. 11873–11877, "Cloning, function expression, and characterization of human prostaglandin E2 receptor EP2 subtype".

Rodan et al., Endocrinology, vol. 121 (1987), pp. 1917–1923, "Growth stimulation of rat calvaria osteoblastic cells by acidic fibroblast growth factor".

Abramovitz et al., Advances in Prostaglandin, Thromboxane, and Leukotriene Res., vol. 23 (1995), pp. 499–504, Human prostanoid receptors: Cloning and characterization.

(List continued on next page.)

Primary Examiner—Theodore J. Criares
(74) Attorney, Agent, or Firm—James M. Hunter, Jr.; Mark R. Daniel

(57) ABSTRACT

The present invention relates to methods for inhibiting bone resorption in a mammal comprising administering to a mammal in need thereof a therapeutically effective amount of an $EP_4$ receptor subtype antagonist.

5 Claims, No Drawings

OTHER PUBLICATIONS deLarco et al., J. Cell. Physiol., vol. 94 (1978), pp. 335–342, "Epithelioid and fibroblastic rat kidney cell clones: epidermal growth factor (EGF) receptors and the effect of mouse sarcoma virus transformation".

Chomczynski et al., Anal. Biochem., vol. 162 (1987), pp. 156–159, "Single–step method of RNA isolation by acid guanidinium thiocyanate–phenol–chloroform extraction".

Weinreb et al., J. of Bone & Min. Res., vol. 5 (1990), pp. 831–842, "Different pattern of alkaline phosphatase, osteopontin, and osteocalcin exrpession in developing rat bone visualized by in situ hybridization".

Shinar et al., J. of Bone & Min. Res., vol. 8 (1993), pp. 403–414, "Expression of αv and β3 integrin subunits in rat osteoclasts in situ".

Ikeda et al., J. Bone & Min. Res., vol. 10 (1995), p. S172, Abstract No. 133, "In situ localization of three subtypes (EP1, EP3 and EP4) of prostaglandin E receptors in embryonic and newborn mice".

Sato et al., HCAPLUS Abstract 1990:132232, J. Bone Min. Res. (1990), vol. 5(1), pp. 31–40, "Effects of bisphosphonates on isolated rat osteoclasts as examined by reflected light microscopy".

Nishigaki et al., Medline Abstract 95278356, FEBS LETTERS (1995), vol. 364(3), pp. 339–341, "Identification of prostaglandin E receptors 'EP2'cloned from mastocytoma cells EP4 subtype".

METHODS FOR INHIBITING BONE RESORPTION

CROSS REFERENCE TO RELATED APPLICATIONS

This application is a divisional of U.S. application Ser. No. 09/416,733, filed Oct. 13, 1999, now U.S. Pat. No. 6,414,006, which claims priority to U.S. Provisional Application Serial No. 60/104,339, filed Oct. 15, 1998, now abandoned, the contents of all of the foregoing of which are hereby incorporated by reference in their entirety.

BRIEF DESCRIPTION OF THE INVENTION

The present invention relates to methods for inhibiting bone resorption in a mammal comprising administering to a mammal in need thereof a therapeutically effective amount of an $EP_4$ receptor subtype antagonist.

BACKGROUND OF THE INVENTION

A variety of disorders in humans and other mammals involve or are associated with abnormal bone resorption. Such disorders include, but are not limited to, osteoporosis, glucocorticoid induced osteoporosis, Paget's disease, abnormally increased bone turnover, periodontal disease, tooth loss, bone fractures, rheumatoid arthritis, periprosthetic osteolysis, osteogenesis imperfecta, metastatic bone disease, hypercalcemia of malignancy, and multiple myeloma. One of the most common of these disorders is osteoporosis, which in its most frequent manifestation occurs in post-menopausal women. Osteoporosis is a systemic skeletal disease characterized by a low bone mass and microarchitectural deterioration of bone tissue, with a consequent increase in bone fragility and susceptibility to fracture. Osteoporotic fractures are a major cause of morbidity and mortality in the elderly population. As many as 50% of women and a third of men will experience an osteoporotic fracture. A large segment of the older population already has low bone density and a high risk of fractures. There is a significant need to both prevent and treat osteoporosis and other conditions associated with bone resorption. Because osteoporosis, as well as other disorders associated with bone loss, are generally chronic conditions, it is believed that appropriate therapy will typically require chronic treatment.

Normal bone physiology involves a process wherein bone tissue is continuously being turned over by the processes of modeling and remodeling. In other words, there is normally an appropriate balance between resorption of existing bone tissue and the formation of new bone tissue. The exact mechanism underlying the coupling between bone resorption and formation is still unknown. However, an imbalance in these processes is manifested in various disease states and conditions of the skeleton.

Two different types of cells called osteoblasts and osteoclasts are involved in the bone formation and resorption processes, respectively. See H. Fleisch, *Bisphosphonates In Bone Disease, From The Laboratory To The Patient*, 3rd Edition, Parthenon Publishing (1997), which is incorporated by reference herein in its entirety.

Osteoblasts are cells that are located on the bone surface. These cells secrete an osseous organic matrix, which then calcifies. Substances such as fluoride, parathyroid hormone, and certain cytokines such as protaglandins are known to provide a stimulatory effect on osetoblast cells. However, an aim of current research is to develop therapeutic agents that will selectively increase or stimulate the bone formation activity of the osteoblasts.

Osteoclasts are usually large multinucleated cells that are situated either on the surface of the cortical or trabecular bone or within the cortical bone. The osteoclasts resorb bone in a closed, sealed-off microenvironment located between the cell and the bone. The recruitment and activity of osteoclasts is known to be influenced by a series of cytokines and hormones. It is well known that bisphosphonates are selective inhibitors of osteoclastic bone resorption, making these compounds important therapeutic agents in the treatment or prevention of a variety of systemic or localized bone disorders caused by or associated with abnormal bone resorption. However, despite the utility of bisphosphonates there remains the desire amongst researchers to develop additional therapeutic agents for inhibiting the bone resorption activity of osteoclasts.

Prostaglandins are alicyclic compounds related to the basic compound prostanoic acid. A natural prostaglandin, $PGE_2$, has the following structure.

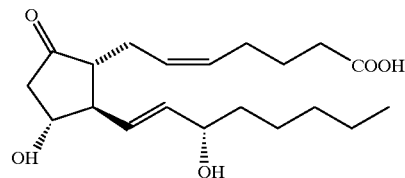

Prostaglandins such as $PGE_2$ are known to stimulate bone formation and increase bone mass in mammals, including man. It is believed that four different receptor subtypes, designated $EP_1$, $EP_2$, $EP_3$, and $EP_4$ are involved in mediating the bone modeling and remodeling processes of the osteoblasts and osteoclasts. The major prostaglandin receptor in bone is $EP_4$, which is believed to provide its effect by signaling via cyclic AMP. However, the scientific information that is currently known about the prostaglandin mediated bone effect is rather limited, because the exact mechanism of action is not known. Prostaglandins and their accosted receptors are more fully described in for example, K. Ono et al., *Important role of $EP_4$, a subtype of prostaglandin (PG) E receptor, in osteoclast-like cell formation from mouse bone marrow cells induced by $PGE_2$, J. of Endocrinology,* 158, R1–R5 (1998), C. D. Funk et al., *Cloning and Expression of a cDNA for the Human Prostaglandin E Receptor EP! Subtype, Journal of Biological Chemistry,* vol. 268, no. 35, pp. 26767–26772 (1993), J. W. Reagan et al., *Cloning of a Novel Human Prostaglandin Receptor with Characteristics of the Pharmacologically Defined $EP_2$ Subtype, Molecular Pharmacology,* vol. 46, pp. 213–220 (1994), J. Yang et al., *Cloning and Expression of the $EP_3$-Subtype of Human Receptors for Prostaglandin $E_2$, Biochemical Biophysical Research Communication,* vol., 198, pp. 999–1006 (1994), L. Bastien et al., *Cloning, Functional Expression and Characterization of the Human Prostaglandin $E_2$ Receptor $EP_2$ Subtype, Journal Biological Chemistry,* vol. 269, pp. 11873–11877 (1994), which are all incorporated by reference herein in their entirety.

In the present invention it is found that antagonists of the $EP_4$ subtype receptor are useful for inhibiting bone resorption. Without being limited by theory, it is believed that these antagonists are responsible for inhibiting the bone resorption activity of the osteoclasts.

It is an object of the present invention to provide methods for inhibiting bone resorption in a mammal comprising administering to a mammal in need thereof a therapeutically effective amount of an $EP_4$ receptor subtype antagonist.

It is another object of the present invention to provide methods for treating or reducing the risk of contracting a disease state or condition in a mammal in need of such treatment or prevention, comprising administering to said mammal a therapeutically effective amount of an $EP_4$ receptor subtype antagonist.

It is another object of the present invention to provide methods for inhibiting bone resorption in a mammal in need thereof comprising administering to said mammal a therapeutically effective amount of an $EP_4$ receptor subtype antagonist and a bisphosphonate active.

It is another object of the present invention to provide pharmaceutical compositions comprising a therapeutically effective amount of an $EP_4$ receptor subtype antagonist.

It is another object of the present invention to provide pharmaceutical compositions comprising a therapeutically effective amount of an $EP_4$ receptor subtype antagonist and a bisphosphonate active.

It is another object of the present invention to identify $EP_4$ receptor subtype antagonists useful for inhibiting bone resorption.

These and other objects will become readily apparent from the detailed description which follows.

SUMMARY OF THE INVENTION

The present invention relates to methods for inhibiting bone resorption in a mammal comprising administering to a mammal in need thereof a therapeutically effective amount of an $EP_4$ receptor subtype antagonist having an $EC_{50}$ value of from about 0.1 nanoM to about 100 microM.

In further embodiments, the present invention relates to methods for treating or reducing the risk of contracting a disease state or condition involving bone tissue in a mammal in need of such treatment or risk reduction, comprising administering to said mammal a therapeutically effective amount of an $EP_4$ receptor subtype antagonist.

In further embodiments, the present invention relates to methods for inhibiting bone resorption in a mammal in need thereof comprising administering to said mammal a therapeutically effective amount of an $EP_4$ receptor subtype antagonist and a bisphosphonate active.

In further embodiments, the present invention relates to pharmaceutical compositions comprising a therapeutically effective amount of an $EP_4$ receptor subtype antagonist.

In further embodiments, the present invention relates to pharmaceutical compositions comprising a therapeutically effective amount of an $EP_4$ receptor subtype antagonist and a bisphosphonate active.

In further embodiments, the present invention relates to a method for identifying antagonists of an $EP_4$ receptor subtype.

In further embodiments, the present invention relates to the use of a composition in the manufacture of a medicament for inhibiting bone resorption in a mammal comprising administering to a mammal in need thereof a therapeutically effective amount of an $EP_4$ receptor subtype antagonist.

All percentages and ratios used herein, unless otherwise indicated, are by weight. The invention hereof can comprise, consist of, or consist essentially of the essential as well as optional ingredients, components, and methods described herein.

DETAILED DESCRIPTION OF THE INVENTION

The present invention relates to methods for inhibiting bone resorption in a mammal comprising administering to a mammal in need thereof a therapeutically effective amount of an $EP_4$ receptor subtype antagonist having an $EC_{50}$ value of from about 0.1 nanoM to about 100 microM.

Prostaglandins E (especially $PGE_2$) stimulate bone formation and increase bone mass in several species, including man. The mechanism of this effect, the target cells and the receptors involved are not completely known. Specific cell-surface receptors for $PGE_2$, such as $EP_{1-4}$, which employ different secondary messenger systems have been cloned and characterized. It is believed that cyclic AMP may have a role in osteogenesis induced by $PGE_2$. The expression of the $EP_2$ and $EP_4$ receptors is found to be involved in cAMP production in the bone tissue of young adult rats (where $PGE_2$ is markedly anabolic), and in various osteoblastic cell lines. Osteoblastic cell lines, RCT-1, RCT-3, TRAB-11 and RP-1, as well as osteoblastic cells harvested from fetal rat bones express $EP_4$ mRNA but not $EP_2$ mRNA. In addition, $EP_4$ mRNA is expressed in tibiae and calvariae of 5-week-old rats while $EP_2$ is not. Treatment of periosteal cells (RP-1) in vitro with $10^{-6}$ M $PGE_2$ increases the level of $EP_4$ mRNA which peaks at 2 hours. Similarly, systemic administration of an anabolic dose of $PGE_2$ (3–6 mg/kg) to young adult rats upregulates the expression of $EP_4$ in tibiae and calvariae, an effect which peaks at 1–2 hours. Using in-situ hybridization it is found that the increased expression of $EP_4$ mRNA in the tibial metaphysis following systemic $PGE_2$ treatment is localized to bone marrow cells.

$EP_4$ is expressed in osteoblastic cells in vitro and in bone marrow putative osteoprogenitor cells in vivo and is upregulated by its ligand, $PGE_2$. Given the presence of $EP_4$ expression in the cells examined and in bone tissue, it is believed that $EP_4$ is the receptor subtype which mediates the anabolic effects of $PGE_2$.

Prostaglandins (especially $PGE_2$) have multiple effects on bone, stimulating both resorption and formation. Systemic administration of $PGE_2$ or $E_1$ to infants and to animals is clearly anabolic, stimulating bone formation and increases bone mass. Also local administration of $PGE_2$ into long bones stimulates new bone formation, suggesting that that $PGE_2$ acts directly on bone tissue to induce osteogenesis. Histological analysis of bones treated with $PGE_2$ indicates that $PGE_2$ increases the number of osteoblasts present on the bone surface, suggesting that prostaglandins act by recruiting osteoblasts from their precursors.

PGEs act on various cells via specific cell-surface receptors divided into 4 subtypes, $EP_{1-4}$, according to their relative sensitivity to selective agonists and antagonists. The receptor subtypes all belong to the G-protein-coupled receptor family and activate different secondary messenger systems such as adenylate cyclase or phospholipase C. Of these 4 receptors, $EP_4$ and $EP_2$ activate adenylate cyclase, $EP_1$ activates phospholipase C, and $EP_3$ either lowers intracellular cAMP levels or activates phospholipase C, depending on the specific spliced variant.

In osteoblastic cells in vitro, $PGE_2$ stimulates both phosphatidylinositol and cyclic AMP transduction pathways. Both $EP_1$ and $EP_4$, found in osteoblastic MC3T3-$E_1$ cells are believed to play a role in the biological action of $PGE_2$ in bone tissue. Also $PGE_1$, a potent inducer of bone formation in humans and other species, increases intracellular cyclic AMP but has no effect on phosphatidylinositol turnover in osteoblastic cells. It is therefor believed that PGE receptors coupled to adenylate cyclases, $EP_2$ and/or $EP_4$, are involved in osteogenesis. It is also believed that the cyclic AMP pathway is involved in the recruitment of osteoblasts from bone marrow cells. Initial characterization of in vivo expression of EP receptors by in situ hybridization shows that in embryonic and neonatal mice $EP_4$ is the major form found in bone tissue, especially in preosteoblasts. See Ikeda T, Miyaura C, Ichikawa A, Narumiya S, Yoshiki S and Suda T, 1995, *In situ localization of three subtypes ($EP_1$, $EP_3$ and $EP_4$) of prostaglandin E receptors in embryonic and newborn mice. J Bone Miner Res* 10 (sup 1):S172, which is incorporated by reference herein in its entirety.

Also, it is found that $EP_4$ but not $EP_2$ mRNA is expressed in adult rat bone tissue and bone-derived cell lines and that expression is stimulated by $PGE_2$.

Analysis of the in vivo expression of PGE receptors shows that $EP_4$ but not $EP_2$ is expressed in total RNA from adult rat tibiae and calvariae. $EP_4$ is believed to be the major adenylate cyclase-coupled $PGE_2$ receptor expressed in osteoblastic cells and in bone tissue. Also, the $EP_4$ receptor subtype is expressed in the bone tissue of young adult rats, in which $PGE_2$ is strongly anabolic.

$EP_4$ mRNA is expressed in osteoblast precursor cells. It is also found in less differentiated bone cell lines such as RCT-1, TRAB-11 and the RP-1 periosteal cells, but not in fibroblasts. It is highly expressed in bone marrow cells that include osteoblast precursor cells, but not in fully mature osteoblasts on the bone surface. It is believed that $PGE_2$ induces osteogenesis via an increase in the number of active osteoblasts present on the bone surface, resulting from the recruitment of osteoblast precursor cells rather than the enhancement of the activity of existing osteoblasts.

It is found that osteoblast precursors are the major target cells for the anabolic effect of $PGE_2$ and that its action in these cells is mediated by $EP_4$. The $EP_4$ receptor subtype is believed to be the major receptor which mediates the effects of $PGE_2$ in bone tissue rats. Induction of $EP_4$ by $PGE_2$ further supports its biological role in the bone tissue and points to a mechanism of autoamplification of PGE action.

Methods of Inhibiting Bone Resorption

The present invention relates to methods for inhibiting bone resorption in a mammal comprising administering to a mammal in need thereof a therapeutically effective amount of an $EP_4$ receptor subtype antagonist.

The methods and compositions of the present invention are useful for both treating and reducing the risk of disease states or conditions associated with abnormal bone resorption. Such disease states or conditions include, but are not limited to, osteoporosis, glucocorticoid induced osteoporosis, Paget's disease, abnormally increased bone turnover, periodontal disease, tooth loss, bone fractures, rheumatoid arthritis, periprosthetic osteolysis, osteogenesis imperfecta, metastatic bone disease, hypercalcemia of malignancy, and multiple myeloma.

In further embodiments, the methods comprise administering a therapeutically effective amount of an $EP_4$ receptor subtype antagonist and a bisphosphonate active. Both concurrent and sequential administration of the $EP_4$ receptor subtype antagonist and the bisphosphonate active are deemed within the scope of the present invention. With sequential administration, the antagonist and the bisphosphonate can be administered in either order. In a subclass of sequential administration the antagonist and bisphosphonate are typically administered within the same 24 hour period. In yet a further subclass, the antagonist and bisphosphonate typically administered within about 4 hours of each other.

The term "therapeutically effective amount", as used herein, means that amount of the $EP_4$ receptor subtype antagonist, or other actives of the present invention, that will elicit the desired therapeutic effect or response or provide the desired benefit when administered in accordance with the desired treatment regimen. A prefered therapeutically effective amount is a bone resorption inhibiting amount.

"Pharmaceutically acceptable" as used herein, means generally suitable for administration to a mammal, including humans, from a toxicity or safety standpoint.

In the present invention, the agonist is typically administered for a sufficient period of time until the desired therapeutic effect is achieved. The term "until the desired therapeutic effect is achieved", as used herein, means that the therapeutic agent or agents are continuously administered, according to the dosing schedule chosen, up to the time that the clinical or medical effect sought for the disease or condition being mediated is observed by the clinician or researcher. For methods of treatment of the present invention, the compounds are continuously administered until the desired change in bone mass or structure is observed. In such instances, achieving an increase in bone mass or a replacement of abnormal bone structure with normal bone structure are the desired objectives. For methods of reducing the risk of a disease state or condition, the compounds are continuously administered for as long as necessary to prevent the undesired condition. In such instances, maintenance of bone mass density is often the objective.

Nonlimiting examples of administration periods can range from about 2 weeks to the remaining lifespan of the mammal. For humans, administration periods can range from about 2 weeks to the remaining lifespan of the human, preferably from about 2 weeks to about 20 years, more preferably from about 1 month to about 20 years, more preferably from about 6 months to about 10 years, and most preferably from about 1 year to about 10 years.

Methods of Identifying Antagonists of the $EP_4$ Receptor Subtype

The present invention also relates to methods for identifying compounds useful as antagonists of the $EP_4$ receptor subtype. Compounds so identified are useful for inhibiting bone resorption.

The present invention relates to a method for identifying compounds which antagonize an $EP_4$ receptor subtype comprising:

a). contacting a putative antagonist of an $EP_4$ receptor subtype with a cell culture; and b). determining the antagonist activity of said putative agonist with a cell culture not contacted with said putative antagonist.

Compositions of the Present Invention

The pharmaceutical compositions of the present invention comprise a therapeutically effective amount of an $EP_4$ receptor antagonist.

These compositions can further comprise a pharmaceutically-acceptable carrier. In further embodiments these compositions also comprise a bisphosphonate active.

$EP_4$ Receptor Subtype Antagonist

The methods and compositions of the present invention comprise an $EP_4$ receptor subtype antagonist.

The term "antagonist" as used herein, is used in its standard meaning to mean a chemical substance that opposed the physiological effects of another substance. In other words, an antagonist is a chemical substance that opposes the receptor-associated responses normally induced by another bioactive agent.

The antagonists useful herein generally have an $EC_{50}$ value from about 0.1 nM to about 100 microM, although antagonists with activities outside this range can be useful depending upon the dosage and route of administration. In a subclass of the present invention, the antagonists have an $EC_{50}$ value of from about 0.01 microM to about 10 microM. In a further subclass of the present invention, the antagonists have an $EC_{50}$ value of from about 0.1 microM to about 10 microM. $EC_{50}$ is a common measure of antagonist activity well known to those of ordinary skill in the art and is defined as the concentration or dose of an antagonist that is needed to produce half, i.e. 50%, of the maximal effect. See also, Goodman and Gilman's, *The Pharmacologic Basis of Therapeutics,* 9th edition, 1996, chapter 2, E. M. Ross, *Pharmacodynamics, Mechanisms of Drug Action and the Relationship Between Drug Concentration and Effect,* which is incoporated by reference herein in its entirety.

Nonlimiting examples of antagonists useful herein are selected fom the group consisting of 5-butyl-2,4-dihydro-4-[[2'-[N-(3-chloro-2-thiophenecarbonyl)sulfamoyl]biphenyl-4-yl]methyl]-2-{2-(trifluoromethyl)phenyl]-1,2,4-triazol-3-one potassium salt, 5-butyl-2,4-dihydro-4-[[2'-[N-(2-methyl-3-furoyl)sulfamoyl]biphenyl4-yl]methyl]-2-[2-(trifluoromethyl)phenyl]-1,2,4-triazol-3-one, 5-butyl-2,4-dihydro-4-[[2'-[N-(3-methyl-2-thiophenecarbonyl)sulfamoyl]biphenyl-4-yl]methyl]-2-[(2-trifluoromethyl)phenyl]-1,2,4-triaol-3-one, 5-butyl-2,4-dihydro-4-[[2'-[N-(2-thiophenecarbonyl)sulfamoyl]biphenyl-4-yl]methyl]-2-[(2-trifluoromethyl)phenyl]-1,2,4-triaol-3-one, 5-butyl-2,4-dihydro-4-[[2'-[N-[2-(methylpyrrole)carbonyl]sulfamoyl]biphenyl-4-yl]methyl]-2-[(2-trifluoromethyl)phenyl-1,2,4-triazol-3-one, and the pharmaceutically acceptable salts thereof, and mixtures thereof.

In the present invention, the antagonists useful herein are compounds that do not contain a cyclopentanone or hydroxycyclopentane ring. In other words, these are non-cyclopentanone and non-hydroxycyclopentane structures.

Bisphosphonates

The methods and compositions of the present invention, can further comprise a bisphosphonate active. The bisphosphonates of the present invention correspond to the chemical formula

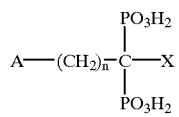

wherein n is an integer from 0 to 7 and wherein A and X are independently selected from the group consisting of H, OH, halogen, $NH_2$, SH, phenyl, C1–C30 alkyl, C3–C30 branched or cycloalkyl, C1–C30 substituted alkyl, C1–C10 alkyl substituted $NH_2$, C3–C10branched or cycloalkyl substituted $NH_2$, C1–C10 dialkyl substituted $NH_2$, C3–C10branched or cycloalkyl disubstituted $NH_2$, C1–C10 alkoxy, C1–C10 alkyl substituted thio, thiophenyl, halophenylthio, C1–C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3–C10 ring.

In the foregoing chemical formula, the alkyl groups can be straight, branched, or cyclic, provided that sufficient atoms are selected for the chemical formula. The C1–C30 substituted alkyl can include a wide variety of substituents, nonlimiting examples which include those selected from the group consisting of phenyl, pyridyl, furanyl, pyrrolidinyl, imidazonyl, $NH_2$, C1–C10 alkyl or dialkyl substituted $NH_2$, OH, SH, and C1–C10 alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

A non-limiting class of structures useful in the instant invention are those in which A is selected from the group consisting of H, OH, and halogen, X is selected from the group consisting of C1–C30 alkyl, C1–C30 substituted alkyl, halogen, and C1–C10 alkyl or phenyl substituted thio, and n is 0.

A non-limiting subclass of structures useful in the instant invention are those in which A is selected from the group consisting of H, OH, and Cl, X is selected from the group consisting of C1–C30 alkyl, C1–C30 substituted alkyl, Cl, and chlorophenylthio, and n is 0.

A non-limiting example of the subclass of structures useful in the instant invention is when A is OH and X is a 3-aminopropyl moiety, and n is 0, so that the resulting compound is a 4-amino-1,-hydroxybutylidene-1,1-bisphosphonate, i.e. alendronate.

Pharmaceutically acceptable salts and derivatives of the bisphosphonates are also useful herein. Nonlimiting examples of salts include those selected from the group consisting alkali metal, alkaline metal, ammonium, and mono-, di, tri-, or tetra-C1–C30-alkyl-substituted ammonium. Preferred salts are those selected from the group consisting of sodium, potassium, calcium, magnesium, and ammonium salts. Nonlimiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those or ordinary skill in the art, reference to a specific weight or percentage of a bisphosphonate compound in the present invention is on an acid active weight basis, unless indicated otherwise herein. For example, the phrase "about 5 mg of a bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid. For other bisphosphonates, the amount of bisphosphonate is calculated based on the corresponding bisphosphonic acid.

Nonlimiting examples of bisphosphonates useful herein include the following:

Alendronic acid, 4-amino-1-hydroxybutylidene-1,1-bisphosphonic acid.

Alendronate (also known as alendronate sodium or alendronate monosodium trihydrate), 4-amino-1-hydroxybutylidene-1,1-bisphosphonic acid monosodium trihydrate.

Alendronic acid and alendronate are described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which are incorporated by reference herein in their entirety.

Cycloheptylaminomethylene-1,1-bisphosphonic acid, YM 175, Yamanouchi (cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and *J. Org. Chem* 32, 4111 (1967), both of which are incorporated by reference herein in their entirety.

1-hydroxy-3-(1-pyrrolidinyl)-propylidene-1,1-bisphosphonic acid (EB-1053).

1-hydroxyethane-1,1-diphosphonic acid (etidronic acid).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-($1^H$-imidazol-1-yl)ethylidene-1,1-bisphosphonic acid (zolendronate).

A non-limiting class of bisphosphonates useful in the instant invention are selected from the group consisting of alendronate, cimadronate, clodronate, tiludronate, etidronate, ibandronate, neridronate, olpandronate, risedronate, piridronate, pamidronate, zolendronate, pharmaceutically acceptable salts thereof, and mixtures thereof.

A non-limiting subclass of the above-mentioned class in the instant case is selected from the group consisting of alendronate, pharmaceutically acceptable salts thereof, and mixtures thereof.

A non-limiting example of the subclass is alendronate monosodium trihydrate.

Other Components of the Pharmaceutical Compositions

The $EP_4$ receptor subtype antagonists, and in further embodiments the bisphosphonate actives and any other additional actives are typically administered in admixture with suitable pharmaceutically acceptable diluents, excipients, or carriers, collectively referred to herein as "carrier materials", suitably selected with respect to the mode of administration. Nonlimiting examples of product forms include tablets, capsules, elixirs, syrups, powders, suppositories, nasal sprays, liquids for ocular administration, formulations for transdermal administration, and the like, consistent with conventional pharmaceutical practices. For example, for oral administration in the form of a tablet, capsule, or powder, the active ingredient can be combined with an oral, non-toxic, pharmaceutically acceptable inert carrier such as lactose, starch, sucrose, glucose, methyl cellulose, magnesium stearate, mannitol, sorbitol, croscarmellose sodium and the like. For oral administration in liquid form, e.g., elixirs and syrups, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated. Suitable binders can include starch, gelatin, natural sugars such a glucose, anhydrous lactose, free-flow lactose, beta-lactose, and corn sweeteners, natural and synthetic gums, such as acacia, guar, tragacanth or sodium alginate, carboxymethyl cellulose, polyethylene glycol, waxes, and the like. Lubricants used in these dosage forms include sodium oleate, sodium stearate, magnesium stearate, sodium benzoate, sodium acetate, sodium chloride and the like. An example of a tablet formulation is that described in U.S. Pat. No. 5,358,941, to Bechard et al, issued Oct. 25, 1994, which is incorporated by reference herein in its entirety. The compounds used in the present method can also be coupled with soluble polymers as targetable drug carriers. Such polymers can include polyvinylpyrrolidone, pyran copolymer, polyhydroxylpropyl-methacrylamide, and the like.

The following Examples are presented to better illustrate the invention.

EXAMPLES

1. Animal Procedures:

For mRNA localization experiments, 5-week old Sprague-Dawley rats (Charles River) are euthanized by $CO_2$, their tibiae and calvariae are excised, cleaned of soft tissues and frozen immediately in liquid nitrogen. For $EP_4$ regulation experiments, 6-week old rats are given a single injection of either vehicle (7% ethanol in sterile water) or an anabolic dose of $PGE_2$ (Cayman Chemical, Ann Arbor, Mich.), 3–6 mg/kg in the same vehicle) intraperitoneally. Animals are euthenized at several time points post-injection and their tibiae and calvariae, as well as samples from lung and kidney tissues are frozen in liquid nitrogen.

2. Cell Cultures

RP-1 periosteal cells are spontaneously immortalized from primary cultures of periosteal cells from tibae of 4-week old Sprague-Dawley rats and are cultured in DMEM (BRL, Gaithersburg, Md.) with 10% fetal bovine serum (JRH Biosciences, Lenexa, Kans.). These cells do not express osteoblastic phenotypic markers in early culture, but upon confluence, express type I collagen, alkaline phosphatase and osteocalcin and produce mineralized extracellular matrix.

RCT-1 and RCT-3 are clonal cell lines immortalized by SV-40 large T antigen from cells released from fetal rat calvair by a cmbination collagenase/hyaluronidase digestion. RCT-1 cells, derived from cells released during the first 10 minutes of digestion (fraction I), are cultured in RPMI 1640 medium (BRL) with 10% fetal bovine serum and 0.4 mg/ml G418 (BRL). These cells differentiate and express osteoblastic features upon retinoic acid treatment. RCT-3 cells, immortalized from osteoblast-enriched fraction III cells, are cultured in F-12 medium (BRL) with 5% Fetal bovine serum and 0.4 mg/ml G418. TRAB-11 cells are also immortalized by SV40 large T antigen from adult rat tibia and are cultured in RPMI 1640 medium with 10% FBS and 0.4 mg/ml G418. ROS 17/2.8 rat osteosarcoma cells are cultured in F-12 containing 5% FBS. Osteoblast-enriched (fraction III) primary fetal rat calvaria cells are obtained by collagenase/hyaluronidase digestion of calvariae of 19 day-old rat fetuses. See Rodan et al., *Growth stimulation of rat calvaria osteoblastic cells by acidic FGF, Endocrinology*, 121, 1919–1923 (1987), which is incorporated by reference herein in its entirety. Cells are released during 30–50 minutes digestion (fraction III) and are cultured in F-12 medium containing 5% FBS.

P815 (mouse mastocytoma) cell, cultured in Eagles MEM with 10% FBS, and NRK (normal rat kidney fibroblasts) cells, cultured in DMEM with 10% FBS, are used as positive and negative controls for the expression of $EP_4$, respectively. See Abramovitz et al., *Human prostanoid receptors: cloning and characterization. In: Samulesson B. et al.* ed) *Advances in prostaglandin, Thrombosznes and leukotriene research*, vol. 23, pp. 499–504 (1995) and de Larco et al., *Epithelioid and fibroblastic rat kidney cell clones: EGF receptors and the effect of mouse sarcoma virus transformation, Cell Physiol.*, 94, 335–342 (1978), which are both incorporated by reference herein in their entirety.

3. Northern Blot Analysis:

Total RNA is extracted from the tibial metaphysis or diaphysis and calvaria using a guanidinium isothiocyanate-phenol-chloroform method after pulverizing frozen bone samples by a tissue homogenizer. See P. Chomczynski et al., *Single-step method of RNA isolation by acid guanidium thiocyanate-phenol-chloroform extraction., Analyt Biochem*, 162, 156–159 (1987), which is incorporated by reference herein in its entirety. RNA samples (20 mg) are separated on 0.9% agarose/formaldehyde gels and transferred onto nylon membranes (Boehringer Mannheim, Germany). Membranes are prehybridized in Hybrisol I (Oncor, Gaithersburg, Md.) and 0.5 mg/ml sonicated salmon sperm DNA (Boehringer) at 42° C. for 3 hours and are hybridized at 42° C. with rat $EP_2$ and mouse $EP_4$ cDNA probes labeled with $[^{32}P]$-dCTP (Amersham, Buckinghamshire, UK) by random priming using the rediprime kit (Amersham). After hybridization, membranes are washed 4 times in 2×SSC+0.1% SDS at room temperature for a total of 1 hour and once with 0.2×SSC+0.1% SDS at 55° C. for 1 hour and then exposed to Kodak XAR 2 film at −70° C. using intensifying screens. After developing the films, bound probes are removed twice with 0.1% SDS at 80° C. and membranes are hybridized with a human GAPDH (Glyceraldehyde 3-Phosphate Dehydrogenase) cDNA probe (purchased from Clontech, Palo Alto, Calif.) for loading control.

4. In-Situ Hybridization:

Frozen tibiae are sectioned coronally at 7 mm thickness and sections are mounted on charged slides (Probe On Plus, Fisher Scientific, Springfield, N.J.) and are kept at −70° C. until hybridization. cRNA probes are labeled with $^{35}S$-UTPgS (ICN, Costa Mesa, Calif.) using a Riboprobe II kit (Promega Madison, Wis.). Hybridization is performed overnight at 50° C. See M. Weinreb et al., *Different pattern of alkaline phosphatase, osteopontin and osteocalcin expression in developing rat bone visualized by in-situ hybridization, J. Bone Miner Res.*, 5, 831–842 (1990) and D. Shinar et al., *Expression of alphav and beta3 integrin subunits in rat osteoclasts in situ*, J. Bone Miner. Res., 8, 403–414 (1993), which are both incorporated by reference herein in their entirety. Following hybridization and washing, sections are dipped in Ilford K5 emulsion diluted 2:1 with 6% glycerol in water at 42° C. and exposed in darkness at 4° C. for 12–14 days. Slides are developed in Kodak D-19 diluted 1:1 with water at 15°, fixed-, washed in distilled water and mounted with glycerol-gelatin (Sigma) after hematoxylin staining. Stained sections are viewed under the microscope (Olympus, Hamburg, Germany), using either bright-field or dark-field optics.

5. Expression of $EP_4$ in Osteoblastic Cell Lines and in Bone Tissue.

The expression of $EP_4$ and $EP_2$ mRNA is examined in various bone derived cells including osteoblast-enriched primary rat calvaria cells, immortalized osteoblastic cell lines from fetal rat calvaria or from adult rat tibia and an osteoblastic osteosarcoma cell line. Most of the osteoblastic cells and cell lines show significant amounts of 3.8 kb $EP_4$ mRNA, except for the rat osteosarcoma cell line ROS 17/2.8. Consistent with this finding, in ROS 17/2.8 cells $PGE_2$ has no effect on intracellular cAMP, which is markedly induced in RCT-3 and TRAB-11 cells. Treatment of RCT-1 cells with retinoic acid, which promotes their differentiation, reduces the levels of $EP_4$ mRNA. NRK fibroblasts do not express $EP_4$ mRNA, while P815 mastocytoma cells, used as positive controls, express large amounts of $EP_4$ mRNA. In contrast to $EP_4$ mRNA, none of the osteoblastic cells and cell lines express detectable amounts of $EP_2$ mRA in total RNA samples. Expression of $EP_4$ mRNA in osteoblastic cells, $EP_4$ is also expressed in total RNA isolated from tibiae and calvariae of 5-week-old rats. In contrast, no $EP_2$ mRNA is found in RNA from tibial shafts.

6. $PGE_2$ Induces the Expression of $EP_4$ mRNA in RP-1 Periosteal Cells and in Adult Rat Tibiae $PGE_2$ enhances its own production via upregulation of cyclooxygenase 2 expression in osteoblasts and in bone tissue thus autoamplifying its own effects. The effect of $PGE_2$ on the levels of $EP_4$ mRNA. RP-1 cells are immortalized from a primary culture of adult rat tibia periosteum is examined. These cells express osteoblast phenotypic makers upon confluence and form mineralized bone matrix when implanted in nude mice. Similar to the other osteoblastic cells examined, RP-1 periosteal cells express a 3.8 kb $EP_4$ transcript. Treatment with $PGE_2$ ($10^{-6}M$) rapidly increases $EP_4$ mRNA levels peaking at 2 hours after treatment. $PGE_2$ has no effect on $EP_4$ mRNA levels in the more differentiated RCT-3 cells. Cell-type specific regulation of $EP_4$ expression by $PGE_2$. $EP_2$ mRNA is not expressed in RP-1 cells before or after treatment with $PGE_2$.

To examine if $PGE_2$ regulates $EP_4$ mRNA levels in vivo in bone tissue, week-old male rats are injected with $PGE_2$ (3–6 mg/Kg). Systemic administration of $PGE_2$ rapidly increased $EP_4$ mRNA levels in the tibialt diaphysis peaking at 2 h after injection. A similar effect of $PGE_2$ on $EP_4$ mRNA is observed in the tibial metaphysis and in calvaria. $PGE_2$ induces $EP_4$ mRNA levels in vitro in osteogenic periosteal cells and in vivo in bone tissue in a cell-specific and tissue-specific manner. $PGE_2$ does not include $EP_2$ mRNA in RP-1 cells nor in bone tissue.

7. Localization of $EP_4$mRNA Expression in Bone Tissue

In situ hybridization is used in order to localize cells expressing $EP_4$ in bone. In control experiment (vehicle-injected) rats, low expression of $EP_4$ was detected in bone marrow cells. Administration of a single anabolic dose of $PGE_2$ increasesd the expression of $EP_4$ in bone marrow cells. The distribution of silver grains over the bone marrow is not uniform and occurs in clumps or patches in many areas of the metaphysis. Within the tibial metaphysis, $EP_4$ expression is restricted to the secondary spongiosa area and is not seen in the primary spongiosa. Hybridization of similar sections with a sense probe (negative control) did not show any signal.

$EP_4$ is expressed in osteoblastic cells in vitro and in bone marrow cells in vivo and is upregulated by its ligand, $PGE_2$.

8. Antagonists of the Present Invention

Using standard methods for measuring antagonist activity, the following compounds are evaluated in cell cultures and in $EP_4$ receptor cell-free systems to determine the antagonist activity of the compounds in terms of their $EC_{50}$ value:

5-butyl-2,4-dihydro-4-[[2'-[N-(3-chloro-2-thiophenecarbonyl)sulfamoyl]biphenyl-4-yl]methyl]-2-{2-(trifluoromethyl)phenyl]-1,2,4-triazol-3-one potassium salt, 5-butyl-2,4-dihydro-4-[[2'-[N-(2-methyl-3-furoyl)sulfamoyl]biphenyl4-yl]methyl]-2-[2-(trifluoromethyl)phenyl]-1,2,4-triazol-3-one, 5-butyl-2,4-dihydro-4-[[2'-[N-(3-methyl-2-thiophenecarbonyl)sulfamoyl]biphenyl-4-yl]methyl]-2-[(2-trifluoromethyl)phenyl]-1,2,4-triaol-3-one, 5-butyl-2,4-dihydro-4-[[2'-[N-(2-thiophenecarbonyl)sulfamoyl]biphenyl-4-yl]methyl]-2-[(2-trifluoromethyl)phenyl]-1,2,4-triaol-3-one, and 5-butyl-2,4-dihydro-4-[[2'-[N-[2-(methylpyrrole)carbonyl]sulfamoyl]biphenyl-4-yl]methyl]-2-[(2-trifluoromethyl)phenyl-1,2,4-triazol-3-one.

9. Pharmaceutical Tablets

Pharmaceutical tablets are prepared using standard mixing and formation techniques.

Tablets containing about 1 to 100 mg of an $EP_4$ receptor subtype antagonist are prepared using the following relative weights of ingredients.

| Ingredient | Per Tablet |
| --- | --- |
| $EP_4$ Receptor Subtype Antagonist | 1 to 100 mg |
| Anhydrous Lactose, NF | 71.32 mg |
| Magnesium Stearate, NF | 1.0 mg |
| Croscarmellose Sodium, NF | 2.0 mg |
| Microcrystalline Cellulose, NF | QS 200 mg |

The resulting tablets are useful for administration in accordance with the methods of the present invention for inhibiting bone resorption.

In further embodiments, tablets are prepared that also contain 5 or 10 mg of a bisphosphonate active, on a bisphosphonic acid active basis, of a bisphosphonate selected from the group consisting of alendronate cimadronate, clodronate, tiludronate, etidronate, ibandronate, neridronate, olpandronate, risedronate, piridronate, pamidronate, zolendronate, and pharmaceutically acceptable salts thereof.

10. Liquid Formulation.

Liquid formulations are prepared using standard mixing techniques.

A liquid formulation containing about 1 to about 100 mg of an $EP_4$ receptor subtype antagonist is prepared using the following relative weights of ingredients.

| Ingredient | Weight |
| --- | --- |
| $EP_4$ Receptor Subtype Antagonist | 1–100 mg |
| Sodium Propylparaben | 22.5 mg |
| Sodium Butylparaben | 7.5 mg |
| Sodium Citrate Dihydrate | 1500 mg |
| Citric Acid Anhydrous | 56.25 mg |
| Sodium Saccharin | 7.5 mg |
| Water | qs 75 mL |
| 1 N Sodium Hydroxide (aq) | qs pH 6.75 |

The resulting liquid formulation is useful for administration for inhibiting bone resorption.

In further embodiments solutions are prepared also containing 5 or 10 mg of a bisphosphonate active, on a bisphosphonic acid active basis, of a bisphosphonate selected from the group consisting of alendronate cimadronate, clodronate, tiludronate, etidronate, ibandronate, neridronate, olpandronate, risedronate, piridronate, pamidronate, zolendronate, and pharmaceutically acceptable salts thereof.

What is claimed is:

1. A pharmaceutical composition comprising a therapeutically effective amount of an $EP_4$ receptor subtype antagonist having an $EC_{50}$ value of from about 0.1 nanoM to about 100 microM and a therapeutically effective amount of a bisphosphonate active.

2. A pharmaceutical composition according to claim 1 wherein said bisphosphonate active corresponds to the chemical structure

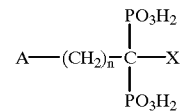

wherein n is an integer from 0 to 7 and wherein A and X are independently selected from the group consisting of H, OH, halogen, $NH_2$, SH, phenyl, C1–C30 alkyl, C3–C30 branched or cycloalkyl, C1–C30 substituted alkyl, C1–C10 alkyl substituted $NH_2$, C3–C10 branched or cycloalkyl substituted $NH_2$, C1–C10 dialkyl substituted $NH_2$, C1–C10 alkoxy, C1–C10 alkyl substituted thio, thiophenyl, halophenylthio, C1–C10 alkyl substituted phenyl, pyridyl, furanyl, pyrrolidinyl, imidazolyl, imidazopyridinyl, and benzyl; or A and X are taken together with the carbon atom or atoms to which they are attached to form a C3–C10 ring; and provided that when n is 0, A and X are not selected from the group consisting of H and OH; and the pharmaceutically acceptable salts thereof.

3. A pharmaceutical composition according to claim 1 wherein said bisphosphonate is selected from the group consisting of alendronate, cimadronate, clodronate, tiludronate, etidronate, ibandronate, neridronate, olpandronate, risedronate, piridronate, pamidronate, zolendronate, pharmaceutically acceptable salts thereof, and mixtures thereof.

4. A pharmaceutical composition according to claim 3 wherein said bisphosphonate is alendronate, pharmaceutically acceptable salts thereof, and mixtures thereof.

5. A pharmaceutical composition according to claim 4 wherein said bisphosphonate is alendronate monosodium trihydrate.

* * * * *